Feb. 16, 1954 G. MERRILL Plant Pat. 1,257

PEACH TREE

Filed Feb. 9, 1953

WITNESS

Madison H. Avery

INVENTOR

Grant Merrill

Lester Nichols

ATTYS.

Patented Feb. 16, 1954

Plant Pat. 1,257

UNITED STATES PATENT OFFICE 1,257

PEACH TREE

Grant Merrill, Red Bluff, Calif.

Application February 9, 1953, Serial No. 336,027

1 Claim. (Cl. 47—62)

This invention relates to a new and distinct variety of peach tree which bears large, firm, brilliantly colored, yellow fleshed, freestone fruit; the fruit generally resembling that of the Candoka peach (United States Plant Patent No. 51), particularly as to the high color and smoothness of the skin.

The primary distinctive characteristic of the present variety of peach tree is a ripening period of the fruit which follows immediately after the harvest of the Rio Oso Gem peach (United States Plant Patent No. 84); the fruit of the instant variety being more highly colored than said Rio Oso Gem.

In addition to its favorable ripening period, as above, another valuable feature of the present variety of peach tree is that the fruit is excellent for long distance commercial shipment, as well as for use as a dessert, culinary, canning, and freezing peach.

The present variety of peach tree is further characterized by flowers which are self-sterile.

The herein claimed variety of peach tree was originated by me in a breeding plot on my ranch located near Red Bluff, county of Tehama, California, in the following manner:

The J. H. Hale peach (unpatented) was crossed with the Levy cling peach (unpatented), and the seeds planted. One of the resulting seedlings, after careful observation, was selected as the most promising. Seeds produced from this tree, from open-pollinated blossoms, were planted and of the resulting seedlings, after careful observation, two were selected as most promising. Seeds from one of these, from open-pollinated blossoms, were planted, and, after careful observation, the best was selected; this latter selection being the present variety. As it is a freestone, and as the clingstone characteristic is recessive, the present variety is believed to have resulted from a cross with one of several neighboring freestone peaches.

Subject to origination of the present variety, in the manner above described, I have successfully asexually reproduced it by grafting onto Golden Jubilee (unpatented) root stock in a test plot on my ranch located as aforesaid. These reproductions were found, upon exacting comparison, to carry forward each and every one of the novel characteristics of the parent tree.

Figures 1, 2:
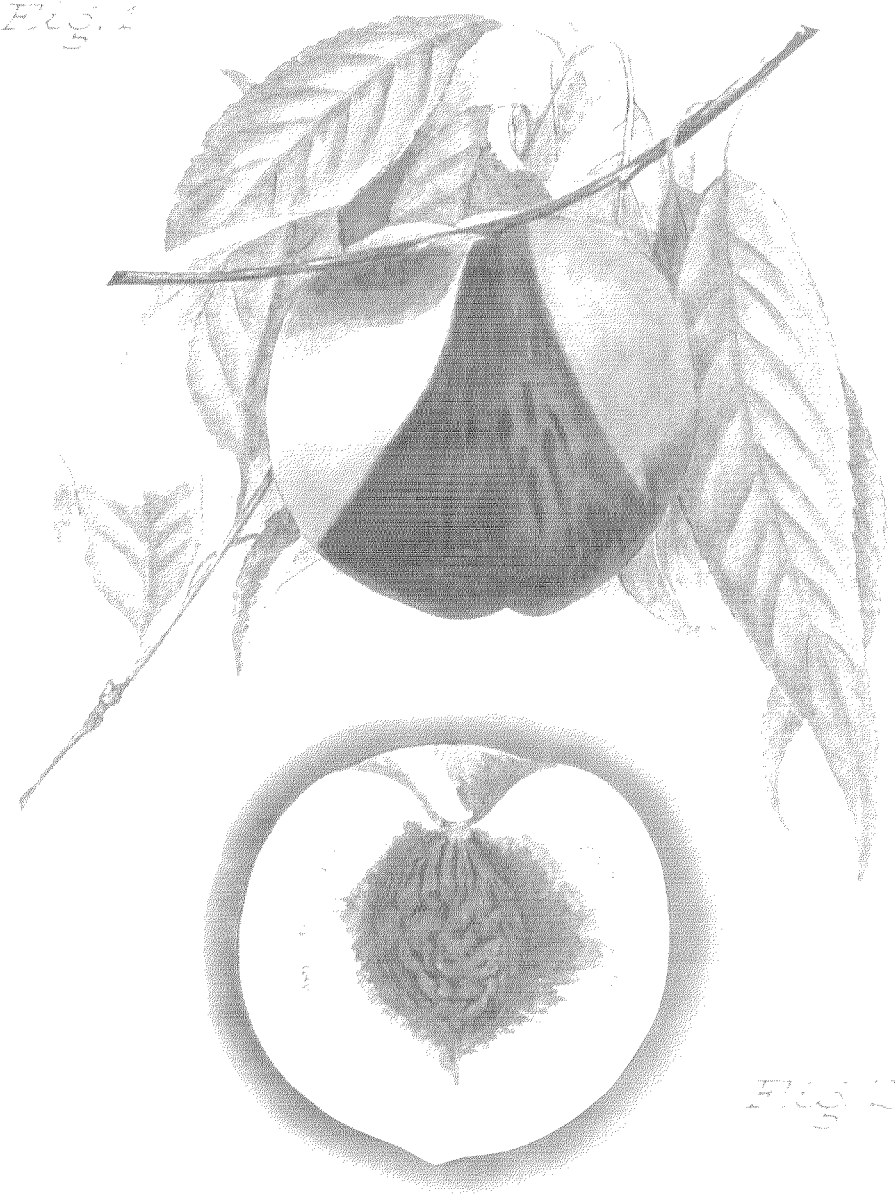
Fig. 1 is an elevation of one of the fruit of the new and distinct variety, together with twigs and leaves.
Fig. 2 is a sectional elevation of one of the fruit, with the stone exposed but remaining in place.

Referring now more specifically to the pomological details of this new and distinct variety of peach tree, the following is an outline description thereof; all major color plate identifications being by reference to Maerz and Paul Dictionary of Color:

Tree: Medium size; medium vigor; upright; open; vasiform; productive; regular bearer.

Trunk: Medium stockiness; medium shagginess.

Branches: Medium stockiness; medium shagginess.

*Color.*—Reddish brown; gray sheen; dull.

*Twigs.*—Medium brown.

*Lenticels.*—Medium quantity; medium size.

Leaves: Medium size. Length—5½" to $8\frac{5}{16}$", average 6⅞". Width—1⅜" to 1⅞", average 1⅝". Medium thickness; slightly rugose.

*Color.*—Top side—medium green (23–L–5). Under side—lighter green (22–J–5).

*Shape.*—Lanceolate.

*Point.*—Acuminate.

*Margin.*—Finely crenate.

*Petiole.*—Medium length; medium thickness.

*Glands.*—Two to seven, average three. Alternate spacing; medium size; reniform shape. Color—green in spring, red in fall. Position—on petiole and base of leaf.

*Stipules.*—On new growth, falling off early.

*Leaf twigs.*—Medium brown (8–J–10).

Flower buds: Medium size; medium length; obtuse; free; pubescent.

Flowers: Date of first bloom—March 14, 1925. Date of full bloom, March 29, 1952. Earliness compared with others, midseason to late. Largely self-sterile. Cross-pollination required.

*Size.*—Small.

*Color.*—Dark pink.

Fruit: First picking at Red Bluff, California, August 15, 1952. Last picking at Red Bluff, California, August 26, 1952. Firm ripe, August 29, 1952.

*Size.*—Uniform; large. Average diameter axially—$2\frac{23}{32}$" to $3\frac{17}{32}$". Transverse in suture plane—$2\frac{29}{32}$" to $3\frac{23}{32}$", average $3\frac{3}{16}$". Diameter transverse cheek to cheek—$2\frac{11}{16}$" to $3\frac{13}{32}$", average $3\frac{1}{32}$".

*Form.*—Uniform; somewhat unsymmetrical; globose.

*Suture.*—A distinct shallow line extending from base to apex; slight depression beyond pistil point.

*Ventral surface.*—Rounded strongly; lipped throughout one side; lips unequal; tendency for one side to be strongly rounded toward apex.

*Cavity.*—Flaring; elongated in suture plane, with suture showing on one side. Average depth—$\frac{9}{16}$''. Average breadth—1''. Markings—yellow under-color, with pink to reddish streaks extending to base.

*Base.*—Mostly truncate, a few slightly oblique.

*Apex.* — Short; slightly rounded. Pistil point—apical.

Skin: Medium thickness; medium tenderness; non-astringent; tenacious to flesh when firm ripe.

*Tendency to crack.*—None in dry season.

*Down.*—Slight; medium length; rolls up when rubbed.

*Color.*—Bright yellow under-color (10–J–5, shading to 11–A–9), with dark red splotches (5–L–11, shading to 7–L–6) covering much of the fruit, except where densely shaded; there being darker streaks or stripes (56–L–1) on such splotches.

Flesh:

*Color.*—Yellow (9–H–1, shading to 9–L–5), with purplish-red (6–L–6) at stone, streaking outwardly and shading lighter (4–L–7) in the flesh.

*Surface of pit cavity.*—Dark red, with dark red fibres shading to pink along tip.

*Amygdalin.*—Moderate.

*Juice.*—Moderate; rich.

*Texture.*—Firm; medium coarseness; meaty.

*Fibres.*—abundant; firm; tender.

*Ripens.*—Evenly. Flesh is very firm when skin is well colored.

*Flavor.*—Subacid; delicate; vinous.

*Aroma.*—Wanting.

*Eating quality.*—Good.

Stone: Free; parts from flesh smoothly.

*Size.* — Medium. Average length — $1\frac{9}{16}$''. Average breadth—$1\frac{1}{16}$''. Average thickness—$\frac{3}{4}$''.

*Form.*—Obovoid; cuneate toward base.

*Base.*—Slightly straight to oblique.

*Hilum.*—Oval.

*Apex.*—Acute.

*Sides.*—Slightly unequal.

*Surface.*—Regularly furrowed near apex; ridged toward apex; pitted toward base.

*Ridges.*—Rounded toward apex.

*Pits.*—Elongated.

*Ventral edge.*—Medium thickness, not winged toward base.

*Color.*—Reddish brown (7–L–12).

*Tendency to split.*—None in dry season.

Use: Long distance shipment; local; dessert; culinary; canning; freezing.

Keeping quality: Good.

Shipping quality: Excellent.

The tree and its fruit herein described may vary in slight detail due to climatic and soil conditions under which the variety may be grown.

Having thus described my invention, I claim:

A new and distinct variety of peach tree, as described and illustrated, bearing large, firm, brilliantly colored, yellow fleshed, freestone fruit; characterized by a ripening period immediately following the Rio Oso Gem peach; by higher colored fruit than said Rio Oso Gem peach; and by fruit which more closely resembles that of the Candoka peach than any other, especially as to color and smoothness of the skin.

GRANT MERRILL.

No references cited.